(12) United States Patent
Wright

(10) Patent No.: US 8,429,950 B2
(45) Date of Patent: Apr. 30, 2013

(54) FIELD OLFACTOMETER WITH DIFFERENTIAL FLOW-BASED DYNAMIC DILUTION

(75) Inventor: Donald Wright, Georgetown, TX (US)

(73) Assignee: Don Wright & Associates, L.L.C., Georgetown, TX (US)

( * ) Notice: Subject to any disclaimer, the term of this patent is extended or adjusted under 35 U.S.C. 154(b) by 266 days.

(21) Appl. No.: 12/851,432

(22) Filed: Aug. 5, 2010

(65) Prior Publication Data

US 2011/0030450 A1 Feb. 10, 2011

Related U.S. Application Data

(60) Provisional application No. 61/273,597, filed on Aug. 6, 2009.

(51) Int. Cl.
*G01N 33/497* (2006.01)
(52) U.S. Cl.
USPC ........................................................ 73/23.34
(58) Field of Classification Search .................. 73/23.34
See application file for complete search history.

(56) References Cited

U.S. PATENT DOCUMENTS

| | | | |
|---|---|---|---|
| 2,327,060 | A | 8/1943 | Pollak et al. |
| 2,837,912 | A | 6/1958 | Moncrieff |
| 3,618,359 | A | 11/1971 | Randebrock et al. |
| 3,882,713 | A | 5/1975 | Nishida et al. |
| 4,488,439 | A * | 12/1984 | Gast et al. ................. 73/861.18 |
| 5,996,396 | A | 12/1999 | Marshall et al. |
| 6,006,583 | A | 12/1999 | Hayashi |
| 6,018,984 | A | 2/2000 | McGinley et al. |
| 6,067,842 | A | 5/2000 | Gygax et al. |
| 6,196,051 | B1 | 3/2001 | Marshall et al. |

(Continued)

OTHER PUBLICATIONS

Bluyssen, Philomena M., "Air Quality Evaluated with the Human Nose," Air Infiltration Review, Sep. 1991, pp. 5-9, vol. 12, No. 4, The Netherlands (5 pages).

(Continued)

*Primary Examiner* — Lisa Caputo
*Assistant Examiner* — Punam Roy
(74) *Attorney, Agent, or Firm* — Russell D. Culbertson; The Culbertson Group, P.C.

(57) ABSTRACT

A field olfactometer includes a mixing chamber connected to a mask. A sample flow path is defined through the olfactometer as is a diluent flow path. The sample flow path extends from a sample air inlet to a sample air outlet which is open to the mixing chamber. The diluent flow path extends from a diluent air inlet to a diluent air outlet which is also open to the mixing chamber. The sample flow path and diluent flow path are isolated from one another so that the sample air flowing through the sample flow path and diluent air flowing through the diluent flow path cannot mix until the two streams of air exit their respective flow path and enter the mixing chamber where the two streams mix thoroughly prior to reaching the mask. The diluent flow path includes a filter medium to remove odor-causing chemicals from ambient air drawn through the diluent flow path. A flow indicator arrangement provides a suitable indication when the flow rate at one or more points in the olfactometer reaches a predetermined value corresponding to a target dilution of diluent air to sample air. Different flow characteristics along the sample flow path as compared to the diluent flow path produces a gradually decreasing dilution ratio as a user inhales nasally at an increasing rate through the mask.

19 Claims, 6 Drawing Sheets

U.S. PATENT DOCUMENTS

| | | |
|---|---|---|
| 6,595,037 B2 | 7/2003 | McGinley |
| 7,143,631 B2 | 12/2006 | Nurcombe |
| 2001/0011473 A1 | 8/2001 | Marshall et al. |

OTHER PUBLICATIONS

Barnebey-Cheney Company, "Odor Control with Activated Carbon," Journal of the Air Pollution Control Association, May 20-24, 1962, vol. 13, No. 4, Columbus, Ohio (2 pages).

Barnebey & Sutcliffe Corporation, "Scentometer: An Instrument for Field Odor Measurement," Bulletin T-748, 1987, pp. 1-3, Columbus, Ohio (3 pages).

Henry et al.,"Mask Scentometer for Assessing Ambient Odors," Jun. 20-23, 2010 American Society of Agricultural and Biological Engineers, St. Joseph, Michigan (14 pages).

McGinley et al., "Comparison of Field Olfactometers in a Controlled Chamber using Hydrogen Sulfide as the Test Odorant," Sep. 14-17, 2003, St. Croix Sensory, Inc., Lake Elmo, Minnesota (13 pages).

\* cited by examiner

FIELD OLFACTOMETER WITH DIFFERENTIAL FLOW-BASED DYNAMIC DILUTION

CROSS-REFERENCE TO RELATED APPLICATION

The Applicant claims the benefit, under 35 U.S.C. §119(e), of U.S. Provisional Patent Application Ser. No. 61/273,597, filed Aug. 6, 2009, entitled "Continuously Variable Field Transportable Audible Flow Alarmed Dynamic Dilution Olfactometer Device For Environmental Odor Assessment," the entire content of which is incorporated herein by this reference.

This invention was made with government support under SBIR grant No. 2007-33610-18619 awarded by the USDA. The Government has certain rights in the invention.

TECHNICAL FIELD OF THE INVENTION

The invention includes a low-cost field olfactometer that may be used to determine when an environmental odor is present in the ambient air in an amount which is at or above a predetermined dilution ratio. The invention also encompasses a method of olfactometry and a replaceable diluent filter cartridge assembly employed in the olfactometer and olfactometry method.

BACKGROUND OF THE INVENTION

Field olfactometers are used to assess environmental odors, for example, odors from agricultural or industrial operations. Under some regulatory schemes, odors which may emanate from a commercial operation must be controlled to a certain level. An odor level is commonly defined for regulatory purposes by a volumetric dilution ratio of odor-free air to sample air containing the odor-causing chemical or chemicals. In particular, the dilution ratio at which the odor is first detectable by a normal human olfactory system is defined as the dilution to threshold ("D/T") for the odor. A regulatory scheme may require that an odor from a given commercial operation must remain below a certain D/T at a given distance from the operation. For example, the Missouri Air Pollution Control Program Laws and Regulations have historically set the maximum D/T for an odor at a value of 7:1 for emissions from confined animal feeding operations. Also, D/T values below the maximum D/T may be defined as having some other significance in a regulatory scheme. For example, Missouri DNR has also utilized a D/T limit value of 5.4:1 from field screening as an early warning to trigger more extensive laboratory testing.

There are two options for measuring the D/T for an odor that may be emanating from a commercial operation. A first option is to collect sample air at various locations around the operation and then take the collected sample air to a laboratory for analysis using some laboratory-based olfactometry method. However, laboratory-based olfactometry is expensive and thus impractical for many applications. The second option for measuring the D/T for an environmental odor is referred to as field olfactometry. Field olfactometry is performed using a portable field olfactometer which a user may operate to measure the D/T for a given odor at various locations around a commercial operation from which the odor emanates.

Prior field olfactometers include a device known as the Barneby-Sutcliffe Box Scentometer (the "Box Scentometer") which was developed in the 1950s. The Box Scentometer includes a diluent air path having an activated carbon filter, a sample air path, a series of restrictions which may be selected for the sample air path, and two inhalation tubes configured to align with a user's nostrils. In operation, a user places their nostrils against the two inhalation tubes and inhales in order to draw air through the two flow paths. The diluent air path takes ambient air through the activated carbon filter to remove odors. The user first blocks the sample air path and draws air only through the diluent air path to ensure that the device is initially filled with only the filtered, odor-free air. After this initialization, the filtered, odor-free air is used as diluent for the sample air which is then allowed to flow through the sample air path in response to the user's inhalation. Each restriction for the sample air path is an orifice sized to produce a discrete dilution ratio when the user inhales against the inhalation tubes with sufficient force. By operating the Box Scentometer using first the smallest restriction for the sample air path, and then sequentially each larger flow restriction until the odor is detected, the user can identify the D/T for the odor.

The device sold under the trademark Nasal Ranger® is another prior art field olfactometer. The Nasal Ranger olfactometer is fundamentally very similar to the Box Scentometer in that it includes a first flow path for providing filtered, odor-free diluent air, a second path for sample air, and a series of restrictions which may be selected to restrict flow through the sample air path. Rather than the two inhalation tubes employed by the Box Scentometer, the nasal Ranger olfactometer includes a nose mask at an outlet end of the device. The mask provides a seal around the user's nose and allows the user to inhale through their nostrils into the device to draw diluent air and sample air through the device. In the Nasal Ranger olfactometer, the different sample air restrictions are mounted on a dial which the user may rotate so as to align the desired restriction with the sample air path through the device. The Nasal Ranger olfactometer also includes a flow meter which allows the user to see the flow rate through a mixing tube of the device to ensure that the flow rate is at a sufficient level to produce the dilution ratio intended for a given restriction.

As with the Box Scentometer, the user operates the Nasal Ranger olfactometer by first initializing the device with only filtered, odor-free air, and then sequentially using the different sample air restrictions beginning with the smallest flow restriction. The smallest restriction for the sample air path produces the highest dilution ratio in response to a nasal inhalation at a proper rate into the mask of the device. If the odor under assessment is detected when the user inhales at the desired rate with the smallest flow restriction aligned with the sample air path, then the user may record that the D/T of the odor is at least at the dilution ratio produced by operation using the smallest restriction. However, if the odor under assessment is not detected at the dilution ratio produced by the smallest flow restriction in response to a nasal inhalation into the olfactometer at the desired rate, the user rotates the dial to align the next larger restriction with the sample air path and performs another inhalation. The user repeats this operation using sequentially larger flow restrictions until the odor is detected. At the operation at which the odor is detected, the user may record that the odor under assessment is present in the atmosphere at that location and time at a D/T corresponding to the dilution ratio produced using the flow restriction in place for that operation of the olfactometer.

Another prior art field olfactometer is known as the Mask Scentometer. The Mask Scentometer includes a one-quarter face respirator mask with two input cartridges defining two input flow paths. One cartridge is fitted with an activated carbon filter to provide filtered, odor-free air to the mask to serve as a diluent. The other cartridge includes a dial mechanism similar to that employed by the Nasal Ranger olfactometer with a series of different sized orifices. The user may operate the dial to align any one of the different orifices so as to allow sample air to be drawn in to the device through the selected orifice in response to a user's nasal inhalation into the mask. Each orifice which may be selected in the Mask Scentometer correlates to a particular dilution ratio between diluent air provided through the filter cartridge and sample air provided through the second cartridge given a desired total flow rate, that is, a desired user nasal inhalation rate, into the mask.

Aside from the fact that the Mask Scentometer is worn rather than simply manually held against the user's face to provide a seal around the user's nose, the operation of the device is very similar to the operation of the Box Scentometer and Nasal Ranger olfactometer. Once the user ensures that the mask is tilled with odor-free air by blocking the sample air path completely and inhaling filtered, diluent air into the mask, the user moves the dial to align the smallest restriction with the sample air path in the sample air cartridge. The user then inhales through their nostrils into the mask to draw diluent air through the first cartridge and sample air through the second cartridge. If the user detects the odor under assessment with that inhalation, then the user may record that the D/T for the odor is at least at the dilution ratio corresponding to the first, smallest flow restriction and the desired inhalation rate. If the user does not detect the odor with the first inhalation using the first and smallest flow restriction, the user rotates the dial to align the next largest orifice/flow restriction and inhales again. The user continues this process using sequentially larger flow restrictions until the odor is detected. The user may then record that the D/T for the odor under assessment is at the dilution ratio corresponding to the flow restriction in use when the odor is first detected.

There are a number of problems encountered with the prior art field olfactometers. First, the prior art field olfactometers are relatively expensive and thus the devices cannot be widely distributed to allow assessment of odors over large geographical areas and over extended periods of time encompassing a range of environmental conditions. This is a very serious drawback because odor plumes tend to be transient in nature and are variable with weather conditions. Also, with the Box Scentometer and Mask Scentometer, it is difficult to ensure that the nasal inhalation by the user is sufficient to produce the desired flow rate through the two flow paths of the device to result in the intended dilution ratio between diluent air and sample air. Even with the Nasal Ranger olfactometer, which incorporates a flow meter, it is difficult for the user to coordinate their observation of the meter with their operation of the device to ensure that the flow rate through the device is at a level to produce the desired dilution ratio.

SUMMARY OF THE INVENTION

The present invention includes a field olfactometer, an olfactometry method, and a filter cartridge assembly particularly adapted to be used in one preferred form of the field olfactometer.

An olfactometer according to the present invention relies on a user to provide a motive force for drawing ambient air through the device. The user provides this motive force by inhaling through the nostrils with the user's nostrils sealed by a suitable interface to the olfactometer. This interface may be referred to in this disclosure and the accompanying claims as a "human olfaction interface" or simply an "interface," and may comprise a mask that seals to the user's face around the user's nose, structures to seal directly around the user's nostrils, or any other structure that provides a substantial seal to allow the user to inhale through their nostrils and apply that inhalation to draw air through the olfactometer and into the nostrils. The motive force itself required by the present invention is a force generated from the user's inhalation to gradually increase the flow rate through the device. In preferred forms of the invention, the motive force is applied by the user inhaling through the nostrils beginning at a relatively low rate and increasing to a higher rate.

In one preferred form, an olfactometer embodying the principles of the invention includes a mixing chamber connected to the human olfaction interface with a sensing opening providing communication between the mixing chamber and the interface. A sample flow path (first flow path) is defined through the olfactometer as is a diluent flow path (second flow path). The sample flow path extends from a sample air inlet to a sample air outlet which is open to the mixing chamber. The diluent flow path extends from a diluent air inlet to a diluent air outlet which is also open to the mixing chamber. The sample flow path and diluent flow path are isolated from one another so that the sample air flowing through the sample flow path and diluent air flowing through the diluent flow path cannot mix until the two streams of air exit their respective flow path and enter the mixing chamber where the two streams mix thoroughly prior to reaching the human olfaction interface. The diluent flow path includes a filter medium to filter or otherwise remove odor-causing chemicals from ambient air drawn through the diluent flow path. An olfactometer according to the present invention also includes a flow indicator arrangement. The flow indicator arrangement provides a suitable indication when the flow rate at one or more points in the olfactometer reaches a predetermined value correlating to a target dilution representing the ratio of the flow rate through the diluent flow path to the flow rate through the sample flow path in response to the motive force applied at the human olfaction interface.

Due to the differences between the sample flow path and diluent flow path, the resistance to flow through the diluent flow path is different from the resistance to flow through the sample flow path. In particular, the resistance to flow through the diluent flow path increases at a higher rate than the resistance to flow through the sample path in response to the motive force applied at the human olfaction interface. This relative difference between the resistance to flow through the two flow paths is such that the dilution ratio of diluent air (diluent air flow rate) to sample air (sample air flow rate) gradually decreases from a relatively high value at the beginning of the motive force applied by the user, to a relatively low value. The range of dilution ratios which is produced over the course of the motive force includes the target dilution ratio. In this way the olfactometer is configured to produce an indication through the flow indicator arrangement when the olfactometer produces the target dilution ratio and allows the user to determine if the odor under assessment is detectable at that target dilution ratio or a higher dilution ratio.

In one preferred form of the invention, the flow indicator arrangement is adapted to provide at least two different indications, each corresponding to a different dilution ratio of diluent air (diluent air flow rate) to sample air (sample air flow rate). Each indication may correspond to a different target dilution ratio so that the olfactometer may be used to determine if an odor is present at multiple target dilution ratios. As will be discussed below in the illustrative embodiments section, an olfactometer within the scope of the present invention may be configured to provide the two different indications on the application of a single inhalation to provide the motive force, or on different inhalations. Whether the flow indicator arrangement provides one indication or multiple different indications corresponding to different dilution ratios, the indication is preferably an audible indication, but may be a visual indication or any other type of indication.

A filter cartridge assembly embodying the principles of the invention includes a filter body having a volume packed with a suitable filter medium. The filter cartridge assembly also includes a sample air tube extending longitudinally there through. The sample air tube is connected at an inlet end to an inlet plug. The filter body is adapted to be housed in the body of the olfactometer with the sample air tube positioned with the inlet plug received at an inlet end of the olfactometer and providing an inlet opening for the admission of sample air. This configuration of the filter body and integrally mounted sample air tube allows the filter cartridge assembly to be calibrated independently of the remainder of the olfactometer. Thus the filter cartridge assembly may be changed in the olfactometer, as is required periodically due to the limited life of the filter medium, without having to recalibrate the entire olfactometer.

One preferred method of olfactometry according to the present invention includes directing sample air along the sample flow path and directing diluent air along the filtered diluent flow path both to the mixing chamber and both in response to the motive force. As discussed above, the sample flow path provides a first flow resistance that increases at a first rate in response to the motive force, while the second flow path provides a second flow resistance that increases at a second rate in response to the motive force. This preferred method also includes directing sample air from the sample flow path and diluent air from the diluent flow path through the mixing chamber and to an outlet through which the motive force is applied. This method further includes providing a first indication based on the flow rate through one or more of the first flow path, second flow path, or mixing chamber. This first indication correlates to a first target dilution ratio between diluent air flowing through the diluent flow path to sample air flowing through the sample flow path. The second flow resistance and the first flow resistance are selected to provide a dilution ratio between diluent air flowing through the diluent flow path to sample air flowing through the sample flow path which gradually decreases to the first target dilution in response to the motive force.

An olfactometer and method of olfactometry according to the present invention provide a number of advantages over prior field olfactometers and olfactometry methods. One advantage arises from the positive indication produced by the flow indicator arrangement when the target flow rate is produced in the device. By providing an indication, which may preferably be an audible indication, when the flow rate measured at one or more points in the device reaches a level corresponding to a target dilution ratio, the device provides a simple way to determine whether an odor under assessment is present in ambient air at a given dilution ratio for which the olfactometer is calibrated. This dilution ratio may correspond to a dilution ratio having regulatory significance. Another advantage arises from the filter cartridge assembly having an integrated filter body and sample air path. The integrated filter body and sample air path facilitates calibration of the filter cartridge assembly independently of the remainder of the olfactometer. In particular, the integrated filter body and sample air path encompasses two variables affecting the resistance to flow through the diluent and sample flow paths, and this allows each replacement filter cartridge and sample flow path to be fine tuned to produce the desired flow path resistances when installed in the olfactometer. Another important advantage of a field olfactometer according to the present invention, particularly one employing the preferred flow indicator arrangement providing an audible indication, is that the olfactometer is relatively inexpensive to produce as compared to prior art field olfactometer. This reduced cost together with the simplicity of use will facilitate wide distribution of the olfactometer so that data may be gathered over a wide area and window of time suitable for providing a more complete assessment of odors which may emanate from a given odor source.

These and other advantages and features of the invention will be apparent from the following description of the preferred embodiments, considered along with the accompanying drawings.

DESCRIPTION OF ILLUSTRATIVE EMBODIMENTS

Figure 1:
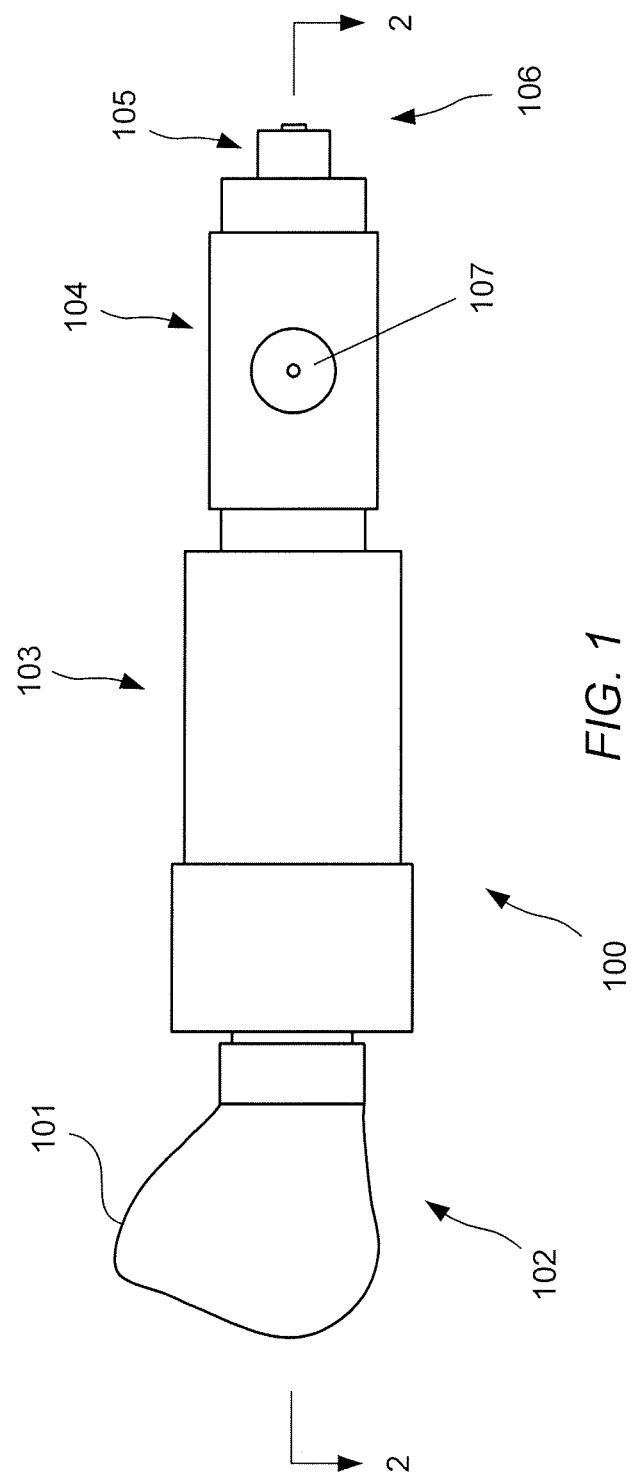
FIG. 1 is a side view of a field olfactometer embodying principles of the present invention.

A field olfactometer 100 embodying the principles of the invention may be described with reference to FIGS. 1 through 3. As shown in FIG. 1, olfactometer 100 includes a mask 101 at an outlet end 102 of the olfactometer. Mask 101 is connected directly to one end of a filter housing 103. The end of filter housing 103 opposite the end connected to mask 101 is connected to a diluent inlet housing 104 which provides an inlet for diluent air into the olfactometer. The inlet for diluent air in this exemplary form of the invention is associated with a flow meter 107 mounted on diluent inlet housing 104. A sample inlet housing 105 is also connected to diluent inlet housing 104 at an inlet end 106 of the olfactometer opposite outlet end 102. As will be discussed below with reference to the section view shown in FIG. 2, the various housings of olfactometer 100 define a sample flow path and a diluent flow path through the device, both of which lead to a mixing chamber which is open to mask 101 through a sensing opening.

Figure 2:
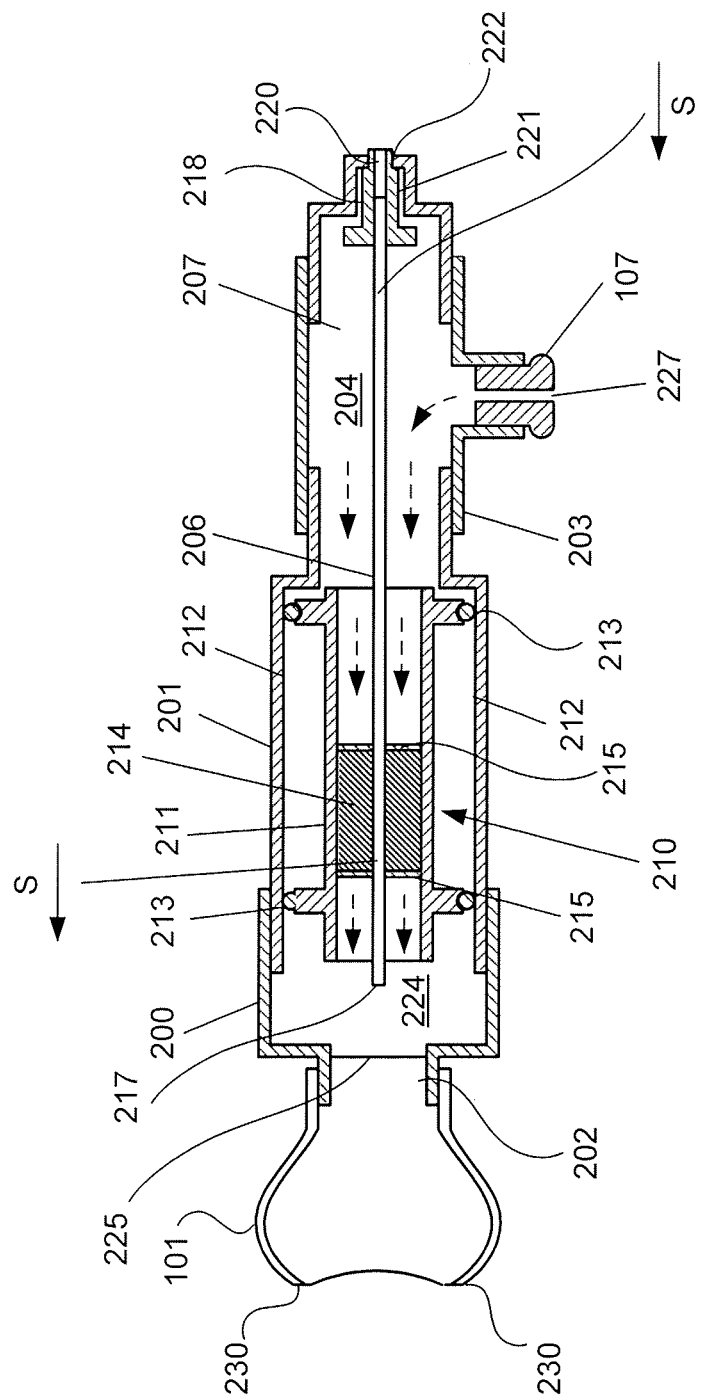
FIG. 2 is a section view taken along line 2-2 in FIG. 1.
Figure 3:
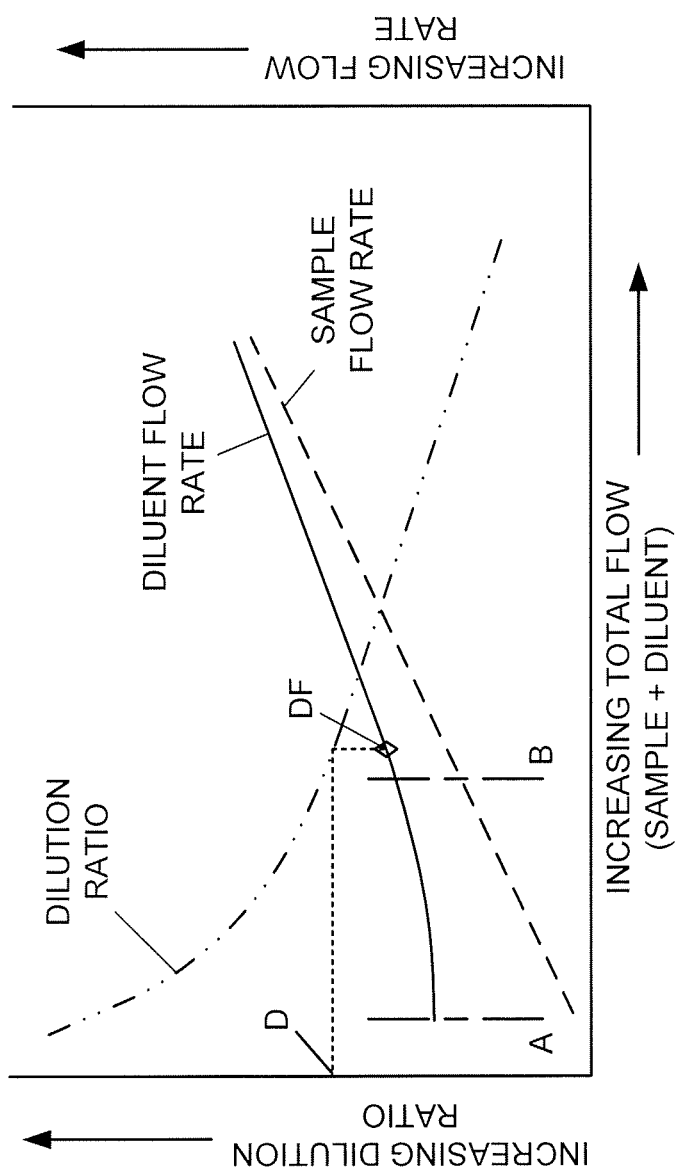
FIG. 3 is a graph showing an example of the relationship between the flow through the diluent flow path and sample flow path according to the present invention, and also showing an example dilution ratio.

Referring to FIG. 2, filter housing 103 includes a first component 200 and a second component 201, both of which are cylindrical in shape. The filter housing first component 200 includes the outlet opening or sensing opening 202 to which mask 101 is connected. Filter housing second component 201 has an opening 203 to which diluent inlet housing 104 is connected. Diluent inlet housing 104 defines an open area 204 that allows the passage of diluent air from flow meter 107 into filter housing 103 through opening 203. Open area 204 also provides room for a sample tube 206 to extend there through from an open area 207 of sample inlet housing 105 through filter housing opening 204.

Olfactometer 100 also includes a filter cartridge 210 mounted within filter housing 103. Filter cartridge 210 includes a cylindrical tube body 211 sealed to the filter housing inner surface 212 with O-rings 213. A filter medium 214 is packed between two perforated retention screens 215 within tubular body 211. Sample tube 206 extends through filter cartridge 210 and includes an outlet end 217 and an inlet end 218. Sample tube inlet end 218 terminates in a passage 220 of a sample inlet plug 221. Sample inlet plug 221 has an end adapted to produce a sealed fit in an opening 222 of sample inlet housing 105. Passage 220 provides an inlet for admitting sample air into sample tube 206. Sample tube outlet end 217 terminates in an area 224 defined within filter housing 103 adjacent to mask 101. This area 224 may be referred to as a mixing chamber because it is in this area that sample air from sample tube 206 and diluent air which passes through filter medium 214 may mix prior to reaching mask 101. The illustrated example olfactometer 100 also includes a perforated mixing screen 225 which includes perforations (not shown due to the scale of the drawing) that help induce turbulence and thereby enhance mixing between sample air and diluent air ahead of mask 101. As will be discussed further below, filter cartridge 210 together with the sample supply tube 206 are part of a replaceable filter cartridge assembly tuned to produce a desired flow rate through two different flow paths through olfactometer 100 in response to a motive force applied through the mask 101 by a user of the olfactometer.

Ambient air to be filtered to produce diluent air enters olfactometer 100 through an opening 227 extending through flow meter 107. Flow meter 107 is adapted to provide an indication when the flow rate through opening 227 reaches a certain value. Although other forms of the invention may use other types of flow meters, the illustrated flow meter 107 is adapted to provide an audible indication when the target flow rate is reached.

After initialization by blocking the sample flow path and drawing only filtered, odor-free air into mixing chamber 224 and mask 101, olfactometer 100 operates in response to a motive force applied by a user through mask 101 by inhaling through the nostrils while the area around the user's nose is sealed against the sealing edge 230 of mask 101. In response to the motive force, that is, a nasal inhalation force to produce a gradual increase in flow rate drawn through the user's nostrils, air flows through two flow paths defined in olfactometer 100. The motive force causes sample air to flow into inlet plug opening 222, and then through sample tube 206 in the direction from the sample tube inlet end 218 to the sample tube outlet end 217. This sample flow path is indicated by arrows S in FIG. 2. The motive force also causes ambient air to flow through flow meter opening 227, into diluent inlet housing area 204, then through filter cartridge 210, and then out of the filter cartridge and into mixing area 224. This diluent flow path is indicated by the dashed line arrows in FIG. 2. It will be noted that although the diluent air is simply ambient air which presumably would also contain the odor under assessment, the filter medium 214 in the diluent flow path removes the odor-causing chemicals from the air and produces substantially odor-free air which enters mixing area 224 to serve as diluent for the sample air.

As the user continues to inhale to gradually increase the flow through the two flow paths indicated by arrows S and the dashed line arrows in FIG. 2, the resistance to flow through the sample path relative to the resistance to flow through the diluent flow path produces a gradually decreasing dilution ratio of diluent air to sample air. This relative change in flow rate through the two flow paths is illustrated in FIG. 3. In particular, at the start of the inhalation producing the motive force for operating the olfactometer, the flow rate through the diluent flow path shown by the dashed line arrows in FIG. 2 is relatively higher than the sample flow rate through the sample flow path shown by arrows S. This corresponds to a relatively high dilution ratio at the start of the inhalation. However, as the flow rate increases over the course of the inhalation, the higher resistance to flow through the diluent flow path as compared to the resistance to flow through the sample flow path causes the flow rate through the diluent flow path to increase at a lower rate than the flow rate through the sample flow path. This is particularly true in the region of flow rate increase between points A and B in FIG. 3. Flow meter 107 is adapted to produce an indication, an audible signal in this example, at a target flow rate DF through the diluent flow path. This target flow rate through the diluent flow path corresponds to a predetermined target dilution ratio shown at D in FIG. 3. Thus if the user detects the odor under assessment at or before the indication produced by flow meter 107, the D/T for the odor is at or above the predetermined target dilution ratio. If the odor under assessment is not detected by the time flow meter 107 produces the indication, then the D/T for the odor is below the target dilution ratio. The target dilution ratio may be set at a regulatory limit so that olfactometer 100 may be used to quickly determine whether an odor is present in the atmosphere at or above the regulatory limit or below the regulatory limit.

The various components of olfactometer 100 may be made of any suitable material. For example, sample tube 206 and sample inlet plug 221 may be made from PTFE, which is preferred for its high resistance to chemical interaction with odor-causing chemicals which may be in the sample air. Mixing screen 225, which may be a 1/16 inch thick sheet of material with 1/16 inch diameter perforations across the entire sheet surface on a 1/8 inch on-center spacing, is also preferably made from PTFE. All of the housing components, filter housing 103, diluent housing 104, and sample inlet housing 105, may be made from PVC. Mask 101 may be made from high purity, odor-free silicone rubber, or from any suitable odor-free plastic or other material that is preferably pliable to provide a comfortable sealing edge 230 for providing the required seal against the user's face around the nose. However, the portion of mask 101 connecting to filter housing 103 may be made from a more rigid plastic or other suitable material. The wall thickness of the various components may be any suitable thickness to provide the desired structural integrity for the device.

Any suitable connections may be used for connecting the various components in the illustrated configuration. Filter housing components 200 and 201 may be connected with a suitable threaded connection, with a female thread formed in first component 200 and a corresponding male thread formed at the end of second component 201. The connections between diluent inlet housing 104 and filter housing 103 on the one end and sample inlet housing 105 on the other may simply be friction connections which are sufficiently tight to provide a good seal. Alternatively, these connections may include a chemical weld or other permanent connecting arrangement since it may not be necessary to separate these components for use or maintenance of olfactometer 100. Any of these connecting arrangements may also be used for connecting mask 101 to filter housing 103. The connection between sample inlet plug 221 and inlet housing opening 222 may simply be a friction connection or a threaded connection, or any other releasable connection that provides a good seal to prevent ambient air from entering open area 207 through opening 222.

The preferred flow meter 107 comprises a vibration-type flow meter which includes an element in or adjacent to opening 227 which is adapted to produce a characteristic vibration and consequent audible indication in response to a desired flow rate through opening 227. The device sold under the trademark Whistle Watch® by Evo Medical Solutions of Adel, Iowa is an example of a suitable vibration-type flow meter which may be employed as flow meter 107. Alternatively, any other suitable flow meter may be used or adapted to be used as a flow indicator arrangement to provide the desired indication at a flow rate through olfactometer 100 corresponding to the target dilution ratio. For example, a floating ball rotometer may be used to provide a visual indication and various electronic flow sensors may be used to control a visual indicator such as an LED, or an electronic sound generating device. Regardless of the particular type of flow meter employed, the flow meter is preferably adjustable so that it may be modified to produce an indication at a desired flow rate within a range of available flow rates. This adjustability allows the flow meter to produce the desired indication at the flow rate correlating to a given target dilution ratio and for a given filter cartridge assembly.

Figure 4:
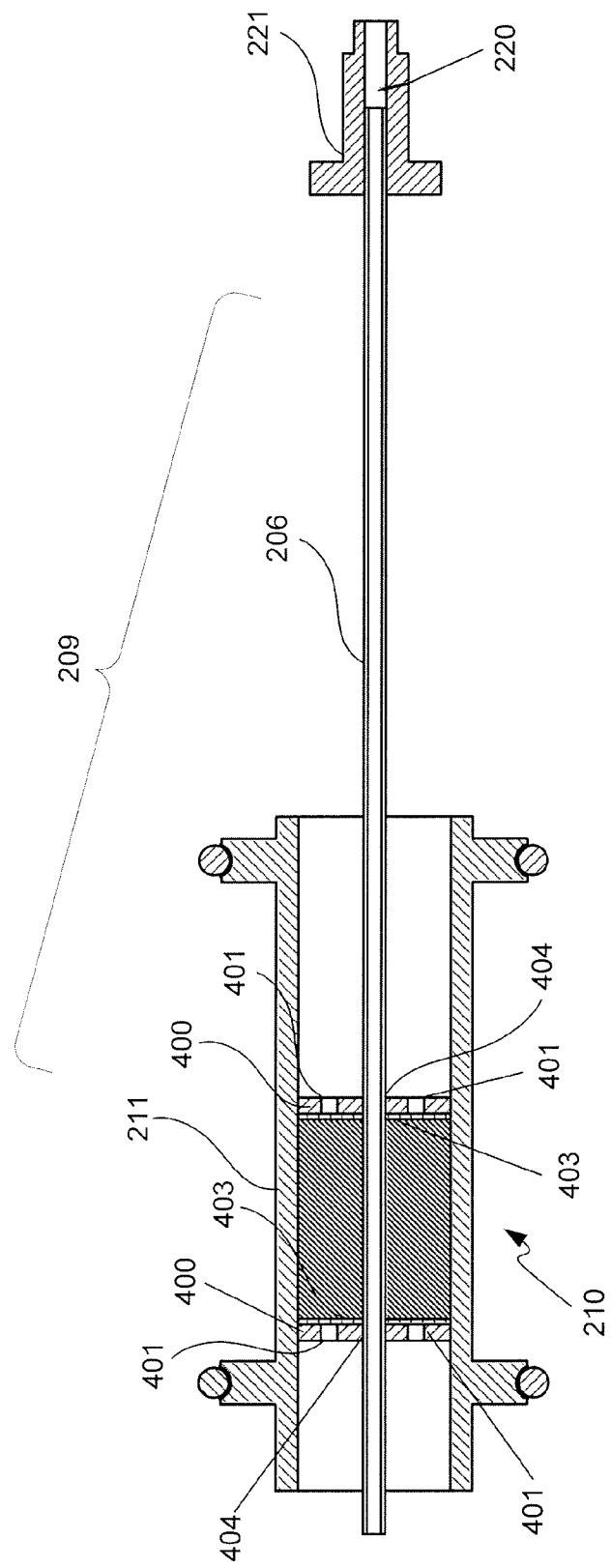
FIG. 4 is an enlarged section view of the integrated filter cartridge and sample flow path shown in the device illustrated in FIG. 2.

FIG. 4 shows further details of the preferred filter cartridge assembly 209 including filter cartridge 210 integrated with sample tube 206 as a unit. The preferred filter medium 214 comprises a medium that results in a relatively consistent flow resistance along the olfactometer diluent flow path when the filter medium must be replaced. One preferred medium includes activated carbon beads having a uniform, generally spherical diameter between approximately 0.40 mm and approximately 0.70 mm. Generally spherical activated carbon beads having a more narrow size distribution range may also be used for the filter medium, for example from approximately 0.45 mm to approximately 0.55 or from approximately 0.55 to approximately 0.65 mm. It is believed that the uniformity of these beads produces the desired consistent flow resistance along the diluent flow path even when the filter medium is replaced. Filter cartridge tube body 211 may be formed from a suitable plastic such as PVC. Retention screens 215 may include PVC disks 400 having several relatively large openings 401 there through, with a suitable permeable retention material sheet 403 facing filter medium 214. A suitable permeable retention material sheet includes a coarse filter disk cut from filter paper stock such as Whatman No. 1 filter paper stock. Sample tube 206 extends through a center opening 404 formed in each disk 400. Openings 404 have close tolerance with the external diameter of sample tube 206 to ensure that the diluent air passes through filter medium 214 in the operation of olfactometer 100 shown in FIGS. 1 and 2.

The preferred integrated filter cartridge assembly 209 including filter cartridge 210 and sample tube 206 has the advantage that it may be tuned independently of the remainder of olfactometer 100 to ensure the desired flow path characteristics in the olfactometer to allow flow meter 107 to produce the desired indication when the flow through the diluent flow path reaches the desired rate. This capability for independent tuning results from three characteristics of olfactometer 100. First, the remainder of olfactometer 100 beyond the integrated cartridge 210 and sample tube 206 is fixed and of known dimensions. Second, when cartridge 210 is reloaded with fresh filter medium, the new filter medium may have a known particle size content and distribution which, given a consistent length of filter medium in cartridge tube body 211, will produce similar flow characteristics in the diluent flow path through olfactometer 100. Third, to the extent the new filter medium produces a slightly different resistance to flow through diluent flow path, the length of sample tube 206 may be modified slightly to make a compensating change in flow resistance through the sample flow path. In addition to or alternatively to modifying the length of the sample tube 206 when filter medium 214 is changed out in cartridge 210, a flow restriction of suitable diameter and length may be inserted into sample tube 206 or elsewhere in the sample flow path to make a compensating change in flow resistance along the sample flow path.

Replaceable filter cartridge assembly 209 may be calibrated using a test-stand (not shown) which includes two intake ports and one vent port. The intake ports correspond to the diluent and sample inlets of olfactometer 100 and facilitate air flow through both the sample tube 206 and the cartridge tube body 211 of the cartridge assembly 209 to be calibrated. The test-stand vent port corresponds to the opening through which the user inhales into olfactometer 100. Utilizing an appropriately regulated vacuum pump connected to apply a vacuum to the test-stand vent port, an individual cartridge may be calibrated by recording parallel flow rate measurements across a target range of vacuum driven total flow values to generate a cartridge-specific calibration curve. Dual, parallel flow measurements can be obtained by visually monitoring dual-tube ball rotometers or, more preferably, dual channel data logging electronic flow meters independently measuring flow rate in each of the diluent flow path and sample flow path. Given that each pathway through the test-stand mounted filter cartridge assembly represents a fixed restriction, once the filter cartridge assembly 209 is calibrated, the flow rate through one pathway, either the sample flow path or the diluent flow path, may be inferred from knowledge of the flow rate in the other pathway. Once the calibration curve for the filter cartridge assembly 209 is produced, the filter cartridge assembly may be removed from the test-stand and inserted into an olfactometer 100. The indicator device of the olfactometer 100, such as flow meter 107 shown in FIGS. 1 and 2, may be adjusted to provide the desired indication at the target flow rate based on the calibration curve produced for the respective filter cartridge assembly 209 on the test-stand. It should be noted that an assembled olfactometer 100 can be calibrated in an analogous manner, substituting a vacuum source attachment assembly for the mask 101.

Figure 5:
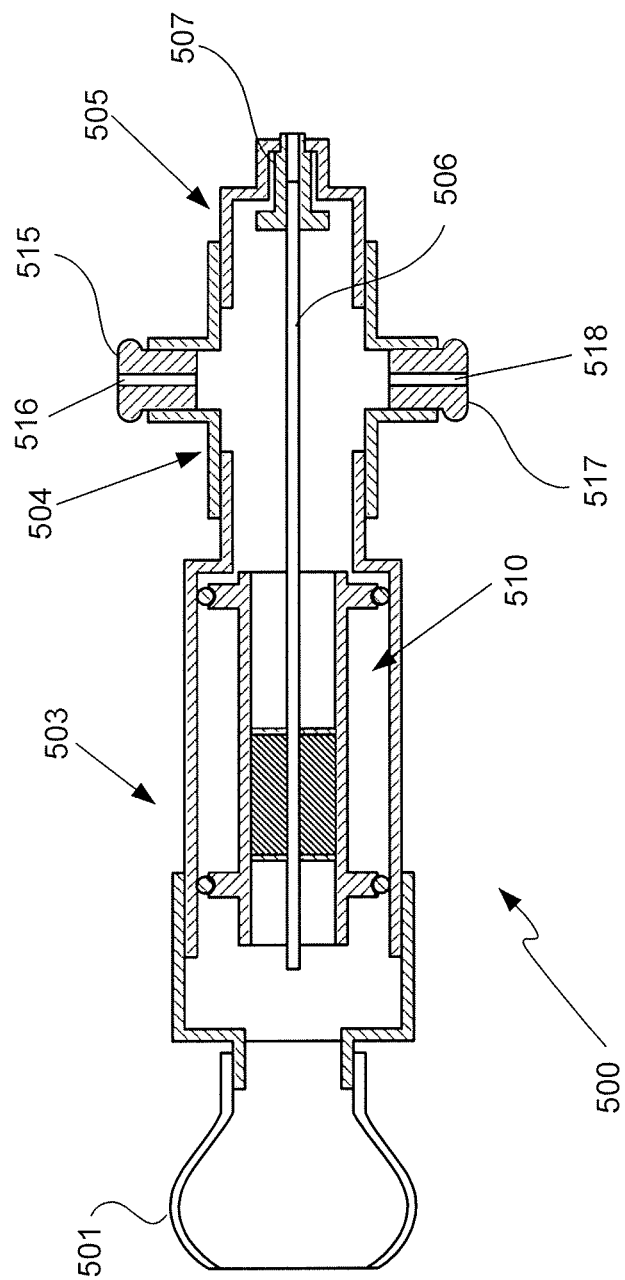
FIG. 5 is a section view similar to FIG. 2, but showing an alternative field olfactometer having two flow meters associated with the diluent flow path.

FIG. 5 shows an alternate field olfactometer 500 within the scope of the present invention. Olfactometer 500 includes a mask 501, filter housing 503, diluent inlet housing 504, and sample inlet housing 505. With the exception of diluent inlet housing 504, each of these components is identical to the corresponding component of olfactometer 100. Olfactometer 500 also includes a filter cartridge assembly including filter cartridge 510 with an integrated sample tube 506 and sample inlet plug 507. These cartridge assembly components are the same as the corresponding components in olfactometer 100. Also, aside from the arrangement of flow meters as will be discussed below, all of the other internal components of olfactometer 500 are the same as the other internal components of olfactometer 100. Because these components are all the same in olfactometer 500 and provide the same functions and advantages, all of these internal components will not be relabeled in FIG. 5.

Olfactometer 500 differs from olfactometer 100 shown in FIGS. 1 and 2 in that the former includes a different flow indicator arrangement. The flow indicator arrangement includes a first flow meter 515 and a second flow meter 517.

First flow meter 515 has a flow meter opening 516 there through, and a second flow meter 517 has a flow meter opening 518 there through. Each of these flow meters 515 and 517 may preferably be of the same type as flow meter 107 described above in connection with olfactometer 100. However, flow meters 515 and 517 are calibrated to provide two distinct indications, each associated with a respective flow rate and correlating to a respective target dilution ratio of diluent air to sample air.

Figure 6:
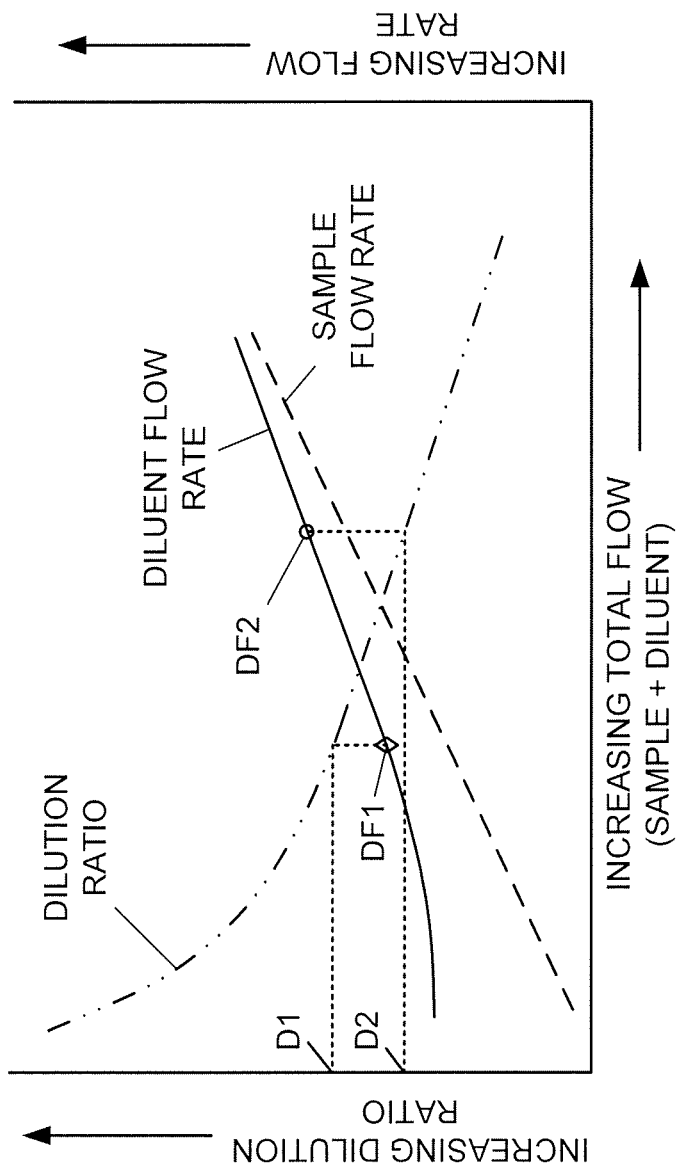
FIG. 6 is a graph similar to that shown in FIG. 3, but showing two different dilution ratios at which an indication may be produced with the olfactometer shown in FIG. 4.

The operation of olfactometer 500 may be described with additional reference to the graph shown in FIG. 6. This graph is similar to the graph of FIG. 3, but includes both a first target dilution ratio D1 which corresponds to a diluent flow rate DF1 and a second target dilution ratio D2 which corresponds to a diluent flow rate DF2. Each target dilution rate corresponds to a respective total flow rate through olfactometer 500 and respective sample and diluent flow rates. It will be noted in reference to FIG. 6 that as the flow rate through the device increases in response to the user's inhalation, the dilution ratio produced by olfactometer 500 gradually decreases to first dilution ratio D1 and then to second dilution ratio D2. One of the flow meters 515 or 517 is adapted to produce an indication (preferably an audible indication) at flow rate DF1 correlating to dilution ratio D1, while the other flow meter is adapted to produce an indication (again preferably audible) at flow rate DF2 corresponding to dilution ratio D2. If the user detects the odor under assessment at or before the time of the first indication, then the user may record that the D/T for the odor is at or above dilution ratio D1. If the user detects the odor under assessment after the first indication but at or before the second indication, then the user may record that the D/T for the odor was between dilution ratio D1 and dilution ratio D2.

Olfactometer 500 may be configured and operated in several different ways to provide the functionality set out in the previous paragraph. In one preferred configuration, the indications correlating to target dilution ratio D1 and target dilution ratio D2 are produced on a single inhalation with no additional manipulation by the user. In this configuration, ambient air flows through each flow meter opening 516 and 518 during the inhalation. Each flow meter 515 and 517 must be adapted to account for the flow through the other flow meter. One of the flow meters is calibrated to produce an indication when the total flow through openings 516 and 518 is at the diluent flow rate DF1 correlating to dilution ratio D1, while the other flow meter is calibrated to produce an indication when the total flow through openings 516 and 518 is at the diluent flow rate DF2 correlating to dilution ratio D2.

An alternate configuration of olfactometer 500 provides the two separate indications on two different operations of the device. In this configuration, a one flow meter 515 or 517 is calibrated to provide the first indication correlating to dilution ratio D1 while the other flow meter is blocked. The remaining flow meter is calibrated to provide the second indication correlating to dilution ration D2 while the first flow meter is blocked. A user would first block the flow meter correlating to the lower dilution ratio D2, and operate the device until the remaining flow meter produced its indication correlating to the higher dilution ratio D1. If the odor was not detected at the higher dilution ratio D1, the user would then block the flow meter correlating to the higher dilution ration D1 and operate the olfactometer until the flow meter correlating to dilution ratio D2 produced its indication correlating to that lower dilution ratio. A simple blocking arrangement comprises a sealing cap adapted to fit over either one of flow meter 515 and 517 or a sealing plug adapted to fit into either one of flow meter opening 516 and flow meter opening 518. Alternatively, the user may simply use one of their fingers to cover the desired flow meter opening.

It should be noted in the single inhalation, dual flow meter configuration described above that the indications, particularly if they are audible indications, should be different in character so that they can be distinguished by the user. For example, one flow meter may be configured to produce an audible indication at a first pitch, while the other flow meter may be configured to produce an audible indication at a second, readily distinguishable pitch. In other examples, one flow meter may be adapted to produce a chirping sound, while the other flow meter may be adapted to produce a whistle. The multiple operation, dual flow meter configuration described above does not require that the two flow meters produce indications of different character so that they can be distinguished, however, the indications may be of different character if that is desired.

Although the invention is described above in connection with specific illustrative embodiments, it will be appreciated that numerous variations on these embodiments are possible within the scope of the present invention. One area of variation relates to the point at which the flow rate is measured to provide the desired indications. Measuring flow rate at the entrance of the air from which diluent will be produced is a preferred location for measuring flow rate because the odor detection remains unaffected by the presence of the flow meter or meters at this location. However, flow rates may be measured in any way and at any point in an olfactometer within the scope of the present invention. Furthermore, flow rates may be measured at multiple locations (in both the diluent flow path and in the mixing chamber, for example) to provide the desired indications.

An olfactometer within the scope of the present invention is also not limited to any particular human olfaction interface. Although olfactometers 100 and 500 are illustrated above with a small mask that is adapted to be manually held to the user's face, other embodiments of the present invention may include straps which allow the device to be worn by the user with the mask providing a hands-free seal to the user's face.

Another variation within the scope of the present invention relates to the mounting and number of flow meters on the olfactometer. Some forms of the invention may have two, three, four, or more flow meters, each adapted to provide an indication at a flow rate correlating to a respective diluent to sample air dilution ratio. The olfactometer may be configured so that all but one of the flow meters is blocked for a given operation of the device. The operation of the olfactometer would then determine whether the odor under assessment was present in the atmosphere at or above the dilution ratio correlated to the indication produced by the one unblocked flow meter. Yet other forms of the invention may include a single flow meter mounted as in olfactometer 100 or otherwise, that is adjustable to provide an indication at any one of multiple different flow rates through the flow meter. Each flow rate at which an indication is provided may correlate to a particular diluent to sample air dilution ratio. An adjustable flow meter may include a setting dial or other arrangement which provides a visual indication of the flow rate, or dilution ratio at which the flow meter is set.

As used herein, whether in the above description or the following claims, the terms "comprising," "including," "carrying," "having," "containing," "involving," and the like are to be understood to be open-ended, that is, to mean including but not limited to. Also, any use of ordinal terms such as "first," "second," "third," etc., in the claims to modify a claim element does not by itself connote any priority, precedence, or order of one claim element over another, or the temporal order in which acts of a method are performed. Rather, unless specifically stated otherwise, such ordinal terms are used merely as labels to distinguish one claim element having a certain name from another element having a same name (but for use of the ordinal term).

The above described preferred embodiments are intended to illustrate the principles of the invention, but not to limit the scope of the invention. Various other embodiments and modifications to these preferred embodiments may be made by those skilled in the art without departing from the scope of the present invention.

The invention claimed is:

1. An olfactometer including:
   (a) a mixing chamber;
   (b) a human olfaction interface having a sensing opening to the mixing chamber;
   (c) a first flow path extending from a sample air inlet to a sample air outlet which is open to the mixing chamber, the first flow path providing a first resistance to flow there through in the direction from the sample air inlet to the mixing chamber;
   (d) a second flow path extending from a diluent air inlet to a diluent air outlet which is open to the mixing chamber, the second flow path being isolated from the first flow path and including a filter medium therein, the filter medium comprising a length of packed spherical adsorbent particles, the length of packed spherical adsorbent particles defining a filtration path forming part of the second flow path, the second flow path providing a second resistance to flow there through in the direction from the diluent air inlet to the diluent air outlet;
   (e) a flow indicator arrangement, the flow indicator arrangement for providing a first indication when a flow rate at one or more points in the olfactometer reaches a predetermined value corresponding to a first target dilution ratio of the flow rate through the second flow path to the flow rate through the first flow path in response to a motive force applied at the human olfaction interface; and
   (f) wherein the second resistance to flow increases at a higher rate than the first resistance to flow in response to the motive force applied at the human olfaction interface so that the dilution ratio of the flow rate through the second flow path to the flow rate through the first flow path gradually decreases to the target dilution ratio in response to the motive force.

2. The apparatus of claim 1 wherein the first indication provided by the flow indicator arrangement is an audible indication.

3. The apparatus of claim 2 wherein the flow indicator arrangement is a vibration-type flow meter.

4. An olfactometer including:
   (a) a mixing chamber;
   (b) a human olfaction interface having a sensing opening to the mixing chamber;
   (c) a first flow path extending from a sample air inlet to a sample air outlet which is open to the mixing chamber, the first flow path providing a first resistance to flow there through in the direction from the sample air inlet to the mixing chamber;
   (d) a second flow path extending from a diluent air inlet to a diluent air outlet which is open to the mixing chamber, the second flow path being isolated from the first flow path and including a filter medium therein, the second flow path providing a second resistance to flow there through in the direction from the diluent air inlet to the diluent air outlet;
   (e) a flow indicator arrangement, the flow indicator arrangement for (i) providing a first indication when the flow rate at one or more points in the olfactometer reaches a predetermined value corresponding to a first target dilution ratio of the flow rate through the second flow path to the flow rate through the first flow path in response to a motive force applied at the human olfaction interface, and for (ii) providing a second indication when the flow rate at one or more points in the olfactometer reaches a predetermined value corresponding to a second target dilution ratio of the flow rate through the second flow path to the flow rate through the first flow path in response to a motive force applied at the human olfaction interface; and
   (f) wherein the second resistance to flow changes at a different rate than the first resistance to flow in response to the motive force applied at the human olfaction interface so that the dilution ratio of the flow rate through the second flow path to the flow rate through the first flow path changes across a range of dilution ratios in response to the motive force, the range of dilution ratios including the first target dilution ratio and the second target dilution ratio.

5. The apparatus of claim 4 wherein the first indication is a first audible indication and the second indication is a second audible indication that is distinguishable from the first audible indication.

6. The apparatus of claim 4 wherein the flow indicator arrangement is mounted in the second flow path so that the first indication and the second indication each provides an indication of the flow rate through the second flow path.

7. The apparatus of claim 4 wherein the flow indicator arrangement includes a first part mounted at a first location in the second flow path and a second part mounted at a second location in the second flow path, and wherein the first part of the flow indicator arrangement provides the first indication and the second part of the flow indicator arrangement provides the second indication.

8. A field olfactometer cartridge assembly including:
   (a) a cartridge enclosure defining an inlet end and an outlet end;
   (b) a sample tube traversing the cartridge enclosure from the inlet to outlet end;
   (c) a filter medium retained in the cartridge enclosure in position to filter odor-causing chemicals from air as the air traverses from the inlet end of the cartridge enclosure to the outlet end of the cartridge enclosure outside of the sample tube;
   (d) a sample inlet plug having a sample passage there through, the sample inlet plug receiving an inlet end of the sample tube therein.

9. The field olfactometer cartridge assembly of claim 8 further including at least one sealing ring mounted on an outer surface of the cartridge enclosure in position to provide a seal against a surface of a housing in which the cartridge enclosure is to be received.

10. The field olfactometer cartridge assembly of claim 8 wherein the filter medium comprises activated carbon beads having a diameter range from approximately 0.40 mm to 0.70 mm.

11. The field olfactometer cartridge assembly of claim 8 wherein the filter medium is packed into an annular area of the cartridge enclosure between the outer wall of the sample tube and inner wall of the cartridge enclosure.

12. The field olfactometer cartridge assembly of claim 11 wherein the filter medium is retained in the cartridge enclosure between two retainer assemblies, each retainer assembly including a disk of material having an outside diameter closely matching an inside diameter of the cartridge enclosure, and also having two or more disk passages extending there through with a sheet of permeable retention material interposed between the disk of material and the filter medium so as to prevent the escape of filter medium through the disk passages.

13. An olfactometer including:
(a) a mixing chamber;
(b) a human olfaction interface having a sensing opening to the mixing chamber;
(c) a first flow path extending from a sample air inlet to a sample air outlet which is open to the mixing chamber, the first flow path providing a first resistance to flow there through in the direction from the sample air inlet to the mixing chamber;
(d) a second flow path extending from a diluent air inlet to a diluent air outlet which is open to the mixing chamber, the second flow path being isolated from the first flow path and including a filter medium therein, the second flow path providing a second resistance to flow there through in the direction from the diluent air inlet to the diluent air outlet;
(e) a flow indicator arrangement, the flow indicator arrangement providing (i) a first indication when a flow rate in the olfactometer reaches a predetermined value corresponding to a first target dilution ratio of the flow rate through the second flow path to the flow rate through the first flow path in response to a motive force applied at the human olfaction interface, and (ii) a second indication when the flow rate in the olfactometer reaches a predetermined value corresponding to a second target dilution ratio of the flow rate through the second flow path to the flow rate through the first flow path in response to the motive force applied at the human olfaction interface, the second target dilution ratio being different from the first target dilution ratio; and
(f) wherein the second resistance to flow increases at a higher rate than the first resistance to flow in response to the motive force applied at the human olfaction interface so that the dilution ratio of the flow rate through the second flow path to the flow rate through the first flow path gradually decreases from an initial dilution ratio, to the first target dilution ratio, and then to the second target ratio in response to the motive force.

14. The apparatus of claim 13 wherein the first indication is a first audible indication and the second indication is a second audible indication that is distinguishable from the first audible indication.

15. The apparatus of claim 13 wherein the flow indicator arrangement is mounted in the second flow path so that the first indication and the second indication each provides an indication of the flow rate through the second flow path.

16. The apparatus of claim 13 wherein the flow indicator arrangement includes a first part mounted at a first location in the second flow path and a second part mounted at a second location in the second flow path, and wherein the first part of the flow indicator arrangement provides the first indication and the second part of the flow indicator arrangement provides the second indication.

17. The apparatus of claim 16 wherein the first part of the flow indicator arrangement is adapted to produce the first indication when the second part of the flow indicator arrangement is blocked to prevent flow there through.

18. An olfactometer including:
(a) a mixing chamber;
(b) a human olfaction interface having a sensing opening to the mixing chamber;
(c) a first flow path extending from a sample air inlet to a sample air outlet which is open to the mixing chamber, the first flow path providing a first resistance to flow there through in the direction from the sample air inlet to the mixing chamber;
(d) a second flow path extending from a diluent air inlet to a diluent air outlet which is open to the mixing chamber, the second flow path being isolated from the first flow path and including a filter medium therein, the second flow path providing a second resistance to flow there through in the direction from the diluent air inlet to the diluent air outlet;
(e) a flow indicator arrangement including (i) a first part mounted in the second flow path to provide a first indication when a flow rate in the second flow path reaches a predetermined value corresponding to a first target dilution ratio of the flow rate through the second flow path to the flow rate through the first flow path in response to a motive force applied at the human olfaction interface, and (ii) a second part mounted in the second flow path so as to provide a second indication when the flow rate through the second flow path reaches a predetermined value corresponding to a second target dilution ratio of the flow rate through the second flow path to the flow rate through the first flow path in response to the motive force applied at the human olfaction interface; and
(f) wherein the second resistance to flow increases at a higher rate than the first resistance to flow in response to the motive force applied at the human olfaction interface so that the dilution ratio of the flow rate through the second flow path to the flow rate through the first flow path gradually decreases to the second target dilution ratio in response to the motive force.

19. The apparatus of claim 18 wherein the first indication is a first audible indication and the second indication is a second audible indication that is distinguishable from the first audible indication.

* * * * *